United States Patent
Hannemann et al.

(10) Patent No.: US 8,716,652 B2
(45) Date of Patent: May 6, 2014

(54) METHOD FOR HOMOGENIZATION OF THE THRESHOLD VALUES OF A MULTI-CHANNEL, QUANTA-COUNTING RADIATION DETECTOR

(75) Inventors: Thilo Hannemann, Erlangen (DE); Steffen Kappler, Effeltrich (DE); Edgar Kraft, Erlangen (DE); Daniel Niederlöhner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 85 days.

(21) Appl. No.: 13/561,690

(22) Filed: Jul. 30, 2012

(65) Prior Publication Data

US 2013/0214144 A1    Aug. 22, 2013

(30) Foreign Application Priority Data

Aug. 9, 2011 (DE) .......................... 10 2011 080 656

(51) Int. Cl.
| | |
|---|---|
| *G01D 18/00* | (2006.01) |
| *G12B 13/00* | (2006.01) |
| *G01T 7/00* | (2006.01) |
| *A61B 6/00* | (2006.01) |

(52) U.S. Cl.
CPC ................. *G01T 7/005* (2013.01); *A61B 6/585* (2013.01)
USPC ................... 250/252.1; 250/370.09; 382/131; 378/207

(58) Field of Classification Search
CPC .......... G01T 7/005; G01T 1/36; A61B 6/582; A61B 6/585; G01N 21/274
USPC ........................................... 250/208.1, 252.1
See application file for complete search history.

(56) References Cited

U.S. PATENT DOCUMENTS

| | | | |
|---|---|---|---|
| 7,479,639 B1 * | 1/2009 | Shahar et al. ............. | 250/370.06 |
| 2005/0105687 A1 | 5/2005 | Heismann et al. | |
| 2007/0023668 A1 * | 2/2007 | Dhurjaty et al. ......... | 250/370.09 |
| 2007/0023669 A1 | 2/2007 | Hefetz et al. | |
| 2008/0048126 A1 | 2/2008 | Janssen et al. | |
| 2011/0012014 A1 * | 1/2011 | Livne et al. ................ | 250/252.1 |

(Continued)

FOREIGN PATENT DOCUMENTS

| | | |
|---|---|---|
| DE | 10212638 A1 | 10/2003 |
| DE | 102006022596 A1 | 11/2007 |
| DE | 102009055807 A1 | 6/2011 |

OTHER PUBLICATIONS

German priority document application No. DE 10 2011 080 656.3 filed Aug. 9, 2011, not yet published.

*Primary Examiner* — David Porta
*Assistant Examiner* — Jeremy S Valentiner
(74) *Attorney, Agent, or Firm* — Harness, Dickey & Pierce

(57) ABSTRACT

A method is disclosed for homogenization of threshold values of a multichannel, quanta-counting radiation detector. In an embodiment of the method empty measurements are carried out with the detector at different spectral compositions of the radiation with different settings of threshold values of the comparators. For each channel of which the comparators is to be set to the same energy threshold, an adapted threshold value is determined for this energy threshold from the empty measurement, at which a variation of the normalized count rate of the channel is minimized over the different spectral compositions of the radiation. This avoids problems in the further processing of the measurement data of the detector, which can occur during alterations of the spectrum.

12 Claims, 3 Drawing Sheets

(56) References Cited

U.S. PATENT DOCUMENTS

| | | |
|---|---|---|
| 2011/0121191 A1 | 5/2011 | Kappler et al. |
| 2011/0233394 A1* | 9/2011 | Glasser et al. ............. 250/252.1 |
| 2012/0087463 A1* | 4/2012 | Greenberg et al. ............... 378/5 |

* cited by examiner

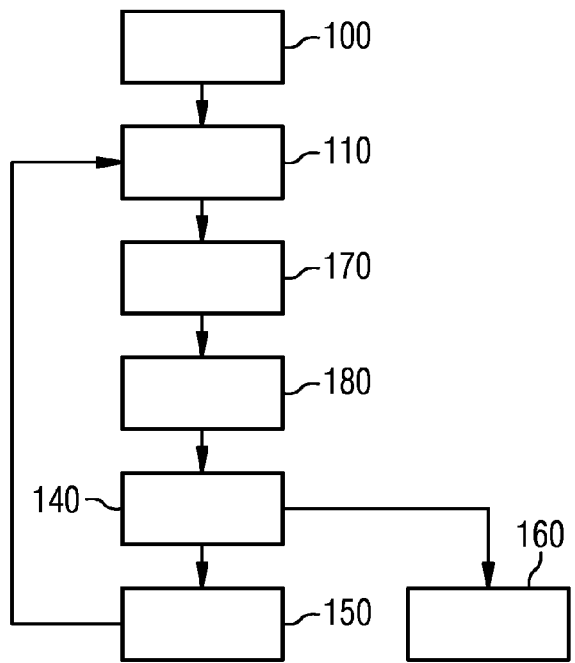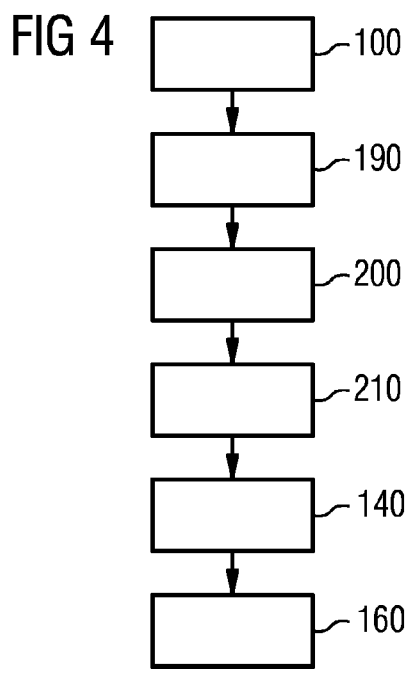

METHOD FOR HOMOGENIZATION OF THE THRESHOLD VALUES OF A MULTI-CHANNEL, QUANTA-COUNTING RADIATION DETECTOR

PRIORITY STATEMENT

The present application hereby claims priority under 35 U.S.C. §119 to German patent application number DE 10 2011 080 656.3 filed Aug. 9, 2011, the entire contents of which are hereby incorporated herein by reference.

FIELD

At least one embodiment of the present invention generally relates to a method for homogenization of the threshold values of a multi-channel, quanta-counting radiation detector, as is used for example in x-ray imaging.

BACKGROUND

A multi-channel detector has a number of detector elements or pixels arranged in rows and columns which form the individual channels of the radiation detector. With a quanta-counting radiation detector a charge pulse is generated for each detected radiation quantum in the respective detector element. The charge pulse is shaped by the detector electronics and the resulting electrical signal is compared in one or more comparators with a threshold value. If the threshold value is exceeded, a counter is incremented. The radiation quanta counted within an integration time produce the measurement signal for the respective comparator channel.

Since the size of the charge pulse depends on the energy of the incident radiation quantum a spectral selection of the counted radiation quanta can be reached via a setting of the electrical threshold level or of the threshold value of the comparator. Only the radiation quanta which as a result of their energy generate an electrical signal which exceeds the threshold value comparator are counted.

Because of variations in the detector elements or pixels and the electronics, the electrical threshold level of the comparator corresponding to a specific energy of the radiation quanta is different for each channel. Thus in the calibration of this type of radiation detector the electronic threshold levels must be set separately for each comparator and each channel so that they correspond to a predetermined energy of the incident radiation quanta. During energy calibration it is determined, for different threshold values of the respective comparator, which energy threshold corresponds to this threshold value. For energy calibration of quanta-counting x-ray detectors radioactive preparations, synchrotron light sources or K fluorescence radiators are used, which emit defined spectral lines or quanta. As a result of the energy calibration each threshold value of the comparator is assigned an energy threshold.

Only a limited accuracy is achieved with the previously known methods for energy calibration however, so that the setting of the threshold levels of the comparators of the radiation detector also only makes possible a restricted accuracy. This results in a dispersion of the actual energetic threshold level over the channels of the detectors, also referred to below as the threshold dispersion. This threshold dispersion has the effect that empty images of the detector measured at different energetic distributions of the incident radiation, also known by the terms "Airscan" or "Flat field image", cannot be converted into one another by a simple scaling of the count rates. The effort for further processing of the measurement data of the detector is significantly increased by this.

SUMMARY

At least one embodiment of the present invention is directed to a method for homogenization of the threshold values of a multichannel quanta-counting radiation detector which makes possible a more precise setting of the threshold values to an energy threshold.

Advantageous embodiments of the method are the subject matter of the dependent claims or can be taken from the subsequent description as well as the example embodiment.

At least one embodiment of the proposed method requires a multichannel quanta-counting radiation detector having at least one comparator with an adjustable threshold value for each channel, wherein the adjustable threshold values of the comparators have been assigned energy thresholds. Preferably a detector is used here with which an energy calibration has already been carried out. In the method empty measurements with different settings of threshold values of the comparators are carried out with the detector for different spectral compositions of the radiation in each case. Empty measurements are to be understood here as carrying out or recording so-called "Airscans" or "Flat field images". With these types of empty measurement no object to be measured is located in the beam path for example for x-ray detectors for x-ray imaging.

BRIEF DESCRIPTION OF THE DRAWINGS

The characteristics, features and advantages of this invention described above, as well as the manner in which these are achieved are explained in a clearer and more easy to understand way in conjunction with the description of the example embodiments given below, which are explained in greater detail in conjunction with the drawings, in which:

FIG. 3 shows a second example of execution sequence of the proposed method, FIG. 4 shows a third example of an execution sequence of the proposed method and FIG. 5 shows a schematic diagram of the components of a quanta-counting multichannel radiation detector.

Figure 1:
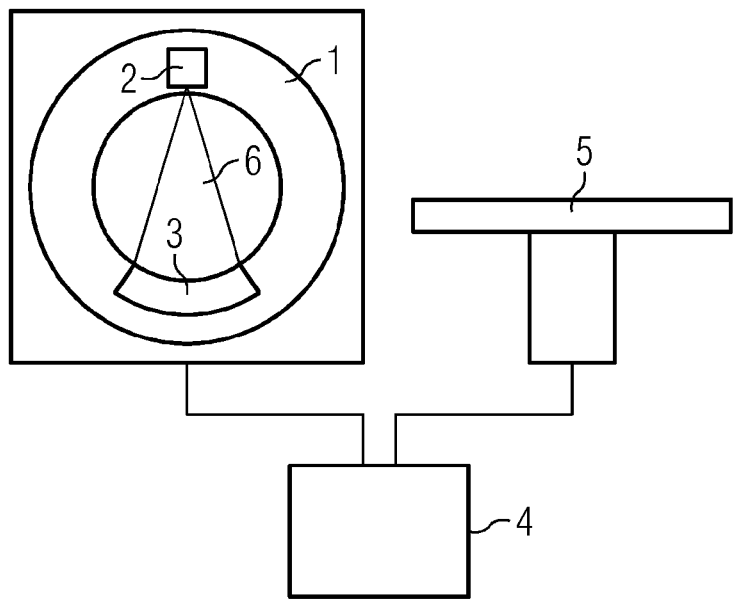
FIG. 1 shows a highly schematic diagram of a computer tomograph with which the method is able to be carried out.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the proposed method requires a multichannel quanta-counting radiation detector having at least one comparator with an adjustable threshold value for each channel, wherein the adjustable threshold values of the comparators have been assigned energy thresholds. Preferably a detector is used here with which an energy calibration has already been carried out. In the method empty measurements with different settings of threshold values of the comparators are carried out with the detector for different spectral compositions of the radiation in each case. Empty measurements are to be understood here as carrying out or recording so-called "Airscans" or "Flat field images". With these types of empty measurement no object to be measured is located in the beam path for example for x-ray detectors for x-ray imaging.

In at least one embodiment of the proposed method an adapted threshold value for this energy threshold is only determined from the empty measurements for each channel of which the comparator is to be set to the same energy threshold, in which a variation of the normalized counting rate of the channel is reduced or minimized by the different spectral compositions of the radiation at which measurements were made. The adapted threshold values determined will then be used in the comparators of the individual channels to adjust them for this energy threshold.

In at least one embodiment of the proposed method the effect of the dependence of the empty image on the spectrum of the incident radiation is thus used as an optimization criterion, in order, by variation of the threshold values, also referred to below because of the way in which they are set, as electrical threshold values, and reduction or minimization of the spectral dependence of the empty image, to reduce the threshold dispersion. This is preferably done in the proposed method starting from a calibration of the electrical threshold levels with one of the known methods by a subsequent homogenization step in which the individual threshold values or threshold levels are adapted accordingly for a predetermined energy threshold. The aim here is to achieve a level of energy threshold for the incident radiation quanta for all observed channels of the detector which is as identical as possible. As an alternative to a prior calibration, the threshold values can also be assigned to the energy thresholds in a different way, for example by setting to a constant DAC value or to x DAC steps above the underlying noise (for the respective energy threshold in each case), in order through this to save the effort for a good calibration.

An embodiment of the method is explained below with reference to the homogenization of the threshold values of an x-ray detector. However embodiments of the method can also easily be transferred to detectors for other types of radiation. It is assumed for the explanations given below that the detector possesses only one comparator per channel and that all channels are to be set to the same energy threshold value. Embodiments of the method can naturally also be directly expanded to a number of comparators and energy thresholds per channel by being executed separately for each energy threshold. The empty measurements in this case can however be carried out in parallel for all energy thresholds. If not all channels are to be set to the same energy threshold, the method can be carried out such that the channels are divided up into groups in accordance with the required energy threshold value and the method is applied separately to each of these groups. Here too the empty measurements can be undertaken in parallel for all groups.

To execute at least one embodiment of the method the detector must be illuminated with at least two different spectral compositions of the x-ray radiation, i.e. with at least two different x-ray energy spectra. This can typically be achieved by different acceleration voltages of the x-ray tubes or by incorporating different filter materials into the beam path. Ideally the alteration of the spectra by filters is undertaken in a manner in which the resulting spectral change between the spectra is similar to one which is produced by inclusion of objects to be examined, since the homogenization of the threshold values of the channels is carried out for precisely this application in x-ray imaging. With specific applications it can be that it is not possible, for example because of a bow-tie filter, to achieve the same spectrum of the incident x-ray radiation at each point of the detector. If the incident spectrum is constant in each case for a number of channels then the method can be carried out once again by group formation on this set of channels, as already explained above. The case of a bow-tie filter in a CT device, it can be assumed for example that the channels of all rows of the same column, i.e. in the direction of advance of the patient table, orthogonal to the modulation of the radiation by the bow-tie filter, see the same input spectrum and thus form one of the groups.

At least one embodiment of the method is directed to setting or adjusting the threshold values or the electrical threshold levels of the individual comparators of the observed channels as exactly as possible, especially more exactly than by a preceding energy calibration that has preferably been carried out beforehand, to an energy threshold of the incident x-ray quanta, e.g. 35 keV, and in doing so to simultaneously achieve homogenization over different spectra. The absolute value of the average energy calibration transfers to the average value of the homogenization. It is thus advantageous to be as accurate as possible in energy calibration at the outset and to carry it out for example with one of the prior art methods cited in the introduction to the description.

At least one embodiment of the method can be carried out in various ways. In a first embodiment the threshold values of the detectors are each set to a value which is produced from the known assignment for a specific energy threshold. Subsequently the first empty measurements are carried out at the different energy spectra of the x-ray radiation and the normalized count rates are calculated in each case for each channel. In the same way further empty measurements will be carried out for the different energy spectra for which the threshold values of the comparators will then be varied. The variation is undertaken until such time as a variation obtained from the normalized count rates, as explained below, of the observed channel in each case is reduced or minimized over the different energy spectra. The threshold values found in this way, also referred to in the present patent application as adapted threshold values, are then used for setting the comparators of these channels at the corresponding energy threshold. The variation of the threshold values for the empty measurements, i.e. from empty measurement to empty measurement for the respective spectrum, is preferably undertaken in accordance with the specification of a minimization algorithm used for this purpose.

The count rates for carrying out at least one embodiment of the proposed method are normalized in an alternate method to a value which is determined from the count rates of all observed channels of the respective energy measurement at the same energy threshold. In this case the simple (arithmetic) mean value of the count rates of the channels can be used. It is also possible however to include a weighted mean value, the median or another quantile for normalization. The use of this normalization makes it possible to include the variants of the respective normalized count rates of each channel over the energy spectra as a measure of distance which is minimized by the variation of the threshold values, preferably via a suitable minimization algorithm. These types of algorithms for minimizing a measure of distance are generally known. This measure of distance has the advantage that, for a division of the detector into modules and carrying out of the method within these modules, only a small amount of information has to be transmitted between modules.

In a further alternative the normalization of the count rate is undertaken in another way. This requires at least three different energy spectra, of which one is used as a reference spectrum. The count rate of each channel, of which the comparator is set to the same threshold level, is now normalized with the count rate of the same channel which was obtained on measurement with the reference spectrum at the same setting of the comparator. In this alternative a deviation of the normalized count rate of the respective channel from the normalized count rates of the other channels, the threshold values of which are set to this energy threshold, can then be used as the distance measure, can be included over the different spectral compositions of the radiation. This distance measure is once again minimized by a minimization algorithm, with this distance measure a better optimization is obtained as a rule than with the distance measure described above, since the minimization algorithm converges more quickly.

At least one embodiment of the proposed method can also be carried out in a second embodiment in another way, since the number of different settings for the electronics threshold levels in a detector is restricted as a rule, typically to <100. This enables the method to be undertaken in the simplest case so that the empty measurements are carried out with all available threshold values in order subsequently to determine the threshold values with the lowest variation of the normalized count rates over the different spectra. The measurements in this case can be made in advance, i.e. before the minimization algorithm runs. The minimization is then undertaken by the algorithm on the data already present.

If fluctuations in the count rate occur because of fluctuations of the x-ray flux emitted by the x-ray source used, for example as a result of fluctuations of the x-ray current, they should be avoided or corrected. The correction can for example be undertaken by additional normalization of the count rates to the signal of a dose monitor. The correction of fluctuations of the emitted x-ray flux must in this case however only be consistent within the measurements with one spectrum, i.e. a spectral dependence of the dose monitor is not a problem and does not have to be corrected.

In a typical CT x-ray detector the choice of size of the detector elements or pixel size is not determined by the resolution to be achieved, but primarily by the maximum count rate of a channel. To enable the expected x-ray flux at the given maximum count rate of the channel to be processed, the pixel size must be selected smaller than would be necessary for the resolution to be achieved. The count results of a number of channels or pixels lying next to each other will then either already be grouped together in the detector itself or in subsequent processing steps. The grouped together pixels lying next to one another form a network, which can be referred to as a macropixel. This grouping of the count rates of a number of pixels opens up the possibility in the present method of increasing the resolution of the electronics threshold of the assembled value or of the macro pixel by dithering in relation to the resolution of the individual thresholds of the pixels. This requires a method which defines the certain point value of the threshold with a higher resolution than is given by the resolution of the threshold setting of the individual channels in the detector used.

At least one embodiment of the proposed method, especially with the distance function mentioned as the second option, is especially well suited for this purpose since this distance function is good for interpolation around its minimum. Starting from a setpoint value of the electronics threshold the actual electronics thresholds of the comparator set of the pixel belonging to a macro pixel are now manipulated so that after the addition or other type of calculation of the count results an effective threshold is produced which approaches the desired target threshold. In the simplest case the electronic thresholds of the respective adjacent channels of the macropixel are selected for this purpose so that the average value of these electronic thresholds lies as close as possible to the target value. If the setting interval of the individual comparators lies for example at 1 keV, then in the grouping together of four channels, an average energy threshold of 40.25 keV can be produced by the energy threshold in three channels being set to 40 keV and in one channel to 41 keV.

In a possible further embodiment of the method this dithering can be incorporated into the optimization. For this purpose the method is first carried out as already described. Then, starting from the threshold values determined, a second pass is executed, in which in each case the grouped count rates of the macropixels, i.e. of the channels of a number of pixels grouped into a common channel, are included. The threshold values of the comparators of the individual channels are selected in this case so that, for each common channel, the desired (average) energy threshold is achieved, and subsequently varied independently of one another. It is important in this second pass to restrict the possible change in the threshold values in relation to the result of the first pass, e.g. to a maximum of one threshold value change. Otherwise there is the danger of for example a threshold of 40 keV being formed from the combination 20 keV+60 keV, which could be numerically correct but adversely affects the energy resolution of the detector. The second pass of the optimization is qualitatively different from the first pass to the extent that optimization now takes place in a multidimensional parameter space, because the thresholds of a number of pixels are included in the optimization. In the first pass only one parameter in each case (the threshold of the individual pixel) is varied.

The proposed method will be explained again in detail below for the preferred area of application, the setting of the threshold values of an x-ray detector in a computer tomograph (CT) or C-arm x-ray device being explained in more detail again on the basis of a number of example embodiments. In these embodiments it is assumed, as it already has been in the preceding explanation, that the x-ray detector only possesses one comparator per channel or detector element or pixel and all channels are to be set to the same energy threshold value. It is further assumed that an energy calibration has already been carried out in this example, by means of k fluorescence counters for example, through which the threshold values or electrical threshold value levels able to be set for the detector have already been assigned energies or energy threshold values.

To carry out an embodiment of the method it is necessary to carry out a number of empty measurements at different spectral distribution of the x-ray radiation with the detector. In this connection FIG. 1 shows a greatly simplified diagram of a computer tomograph, with which the method is able to be carried out. In a known way the computer tomograph has a rotating frame 1 on which an x-ray tube 2 as well as the x-ray detector 3 to be adjusted in the threshold values are disposed. For carrying out the empty measurements, i.e. for a computer tomography, the recording of empty images, the rotating frame 1 is not moved and the patient table 5 is moved out of the recording area of the x-ray system. The x-ray bundle 6 emitted by the x-ray tubes 2 thus ideally strikes the x-ray detector 3 with an x-ray energy distributed over all detector elements. To create the different energy spectra of the x-ray radiation with which the empty images will be recorded, either the acceleration voltage at the x-ray tube 2 can be explicitly changed or different filters can be inserted into the beam path between x-ray tube 2 and x-ray detector 3. The measurement data detected by the x-ray detector 3 is further processed in the control and evaluation unit 4 of the computer tomograph.

Figure 2:
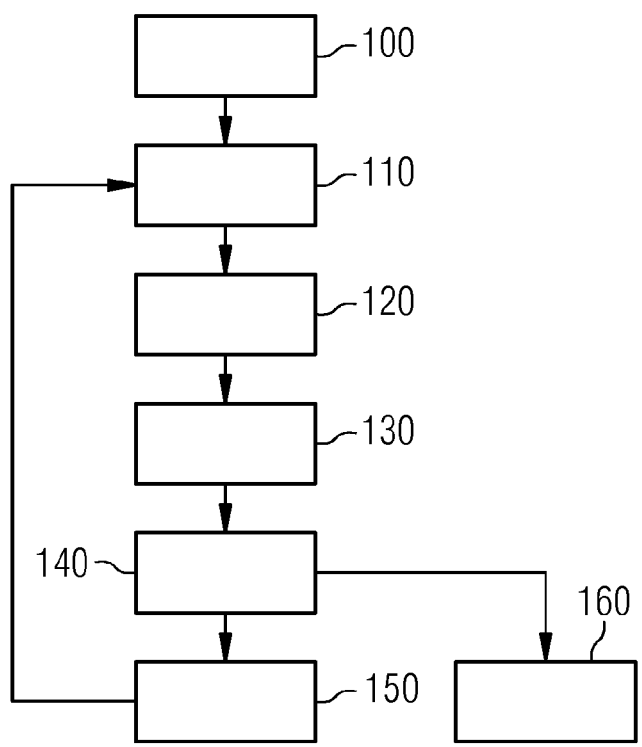
FIG. 2 shows a first example of an execution sequence of the proposed method.

FIG. 2 now shows a first example of method steps for carrying out the proposed method. In a first step 100 each channel is set to the electronic threshold determined from the energy calibration which corresponds to the desired energy threshold. In the next step 110 an empty measurement is carried out with the computer tomograph with at least two different spectral distributions of the x-ray radiation. The count rates of a channel differ for the different spectra since the proportion of photons with an energy above the set threshold of the channel, because of the insufficiently exact energy calibration, differs for the different spectra. In the example of the method shown the count rates of each channel are normalized to the average count rate of all channels of the detectors which are to be set or are set to the same energy threshold. This is done in step 120 of FIG. 2. If all channels already have the same energy threshold with sufficient accuracy, the normalized count rates of each individual channel are constant over the different spectra this channel. If the channel has a deviating energy threshold, then its normalized count rate will vary over the different spectra since it is counting another part of the spectrum from the other channels of the same group. As a result of the plurality of channels of a group or of the detector as a whole, as in the present example, the average count rate used for the normalization can be generally seen as appropriate for the target energy.

The variation of the normalized count rates of a channel over the different spectra serves in the proposed method as a measure of distance which is to be minimized. It is able to be quantified in different ways. In the present example the variants of the normalized count rate over the spectra is used as a measure of distance. This measure of distance has the advantage of a small amount of information only having to be transmitted between the modules if the detector is divided up into modules and the method is carried out within these modules. In step 130 the variance of the count rates of each channel is thus calculated for the example in FIG. 2. This distance function or this measure of distance is minimized via one of the known minimization algorithms in step 140. To this end the empty measurements are repeated with changed electronic thresholds for the channels, with the changing of the electronic thresholds being determined by the minimization algorithm. Step 150 here indicates the change of the threshold values with which the preceding method steps are to be carried out once again. If the minimum of the distance function is determined, in step 160 the comparators of the channels are set to the threshold values at which the minimum of the distance function is produced. For these adapted threshold values the variation of the normalized count rates over the different spectral distributions is minimal so that with this the desired homogenization of the threshold values of the detector is achieved.

Since the minimization of the distance function for each channel can be carried out approximately (except for the influence of this channel on the average value used for normalization) independently of the other channels, the amount of time expended for optimization does not depend on the number of channels. The described method actually functions all the better, the more channels are included in the normalization.

The procedure for homogenization of the threshold values with the aid of the variance as distance function is described once again below in a more general form as a sequence of commands:

For each electronic threshold sw
For each spectrum S
    Record an empty image and store the count values in CS,sw(c) for all channels c.
Correct the count values in accordance with the x-ray dose emitted by the tube for the respective measurement, determined for example by a dose monitor.
For each spectrum S
Determine the average count rate $I_s$ over all channels for the electronic threshold sw0(c) for each channel c, which was determined by the preceding calibration step:

$$I_S = \frac{1}{numberofchannels} \sum_c C_{S,sw0(c)}(c)$$

For each electronic threshold sw
For each channel c
For each spectrum S
Calculate the normalized count rate $N_{S,sw}(c)$:

$$N_{S,sw}(c) = C_{S,sw}(c)/I_S$$

Calculate the variance $\text{var}_{sw}(c)$ of the normalized count rate $N_{S,hd\_sw}(c)$ over the spectra S:

$$\text{var}_{sw}(c) = \sum_{S} (N_{S,sw}(c) - \langle N_{S,sw}(c) \rangle_S)^2$$

For each channel c

Select as the result the threshold sw for which the variance $\text{var}_{sw}(c)$ is minimal.

A further option for quantifying a measure of distance for minimization of the variation of the normalized count rate of the channel over the different spectra is explained below. In this option the count rates are normalized to one of the spectra and a distance function is formed which is produced by the square of the difference between the normalized count rate and the average normalized count rate over all detector channels. This method shows better optimization behavior compared to the methods explained above. When the method is carried out, steps 100 and 110 are executed in the same way as in the example of FIG. 2. Subsequently, in step 170, the normalized count rates are calculated by normalizing the count rate of each channel to the count rate of a reference spectrum which would be obtained for the same setting of the threshold value of the respective comparator or channel. Any given spectrum of the spectra used for the empty measurements is included as a reference spectrum here. The method here however requires the use of at least three different spectra. In the next step 180 the square of the sum of the differences between the respective normalized count rate and the average value of the normalized count rate of the respective empty measurement is then calculated over the measured spectra. Here too this distance measure is reduced by a minimization algorithm 140, wherein the empty measurements are each repeated with the electronic thresholds changed in step 150 for the channels which were specified by the minimization algorithm. This is once again indicated in FIG. 3. If the minimization algorithm 140 has determined the minimum of the measure of distance, the electronic threshold levels or threshold values obtained in this algorithm are used in step 160 to set the comparators or channels of the detector. This corresponds to the procedure of FIG. 2.

Here too this variant of the method is once again presented below in more general form as a sequence of commands:

For each electronics threshold sw
For each spectrum S
Record an empty image and store the count values in $C_{S,sw}(c)$ for all channels c.
Correct the count values in accordance with the x-ray dose emitted by the tube for the respective measurement, determined for example by a dose monitor.
Select a spectrum S0 from the available spectra
For each channel c
For each threshold sw
For each spectrum S
Divide the count values $C_{S,sw}(c)$ by the values $C_{S0,sw}(c)$, that were measured for the spectrum $S_0$. This produces the $S_0$-calibrated count values $C'_{S,sw}$:
$C'_{S,sw}(c) = C_{S,sw}(c)/C_{S0,sw}(c)$
For the spectrum S0 this normalization produces a constant value C'S0,sw of one. In the subsequent calculations this can either be taken into account or the spectrum S0 is removed from the calculations.
For each spectrum S
Determine from the $S_0$-calibrated count values $C'_{S,sw}(c)$ the average $S_0$-calibrated count value $I_S$ over all channels at the electronic threshold for each channel which was determined by the preceding calibration step:

$$I_S = \frac{1}{numberofchannels} \sum_{c} C'_{S,sw0(c)}(c)$$

For each electronic threshold sw
For each channel c
Calculate the square of the sum $d_{sw}(c)$ over the difference between the $S_0$-calibrated count rate $C'_{S,sw}(c)$ and the average $S_0$-calibrated count rate $I_S$ over the spectra S:

$$d_{sw}(c) = \sum_{S} (C'_{S,sw}(c) - I_S)^2$$

For each channel c
Select as a result the threshold for which $d_{sw}(c)$ is minimal.

The known quanta-counting multichannel x-ray detectors only have a restricted number of threshold values or threshold levels available to them to which the comparators of the individual channels can be set. A method sequence is thus described in the example of FIG. 4 in which the empty measurements are carried out in advance and the minimization algorithm subsequently only processes the data available in order to find the (adapted) threshold values with which the smallest variance of the count values is achieved for a predetermined energy threshold over the individual spectra. To this end, in step 190, empty measurements are carried out for different spectra with all possible threshold values. In step 200 the normalized count rates are then calculated in each case and in step 210 the minimization of the measure of distance used is carried out with the minimization algorithm. In this case both the distance measure of FIG. 2 and also the distance measure of FIG. 3 can be used for the minimization of the variation of the count rates over the different spectra. The threshold values determined in such cases are once again used in step 162 to set the comparators of the x-ray detector.

Figure 5:
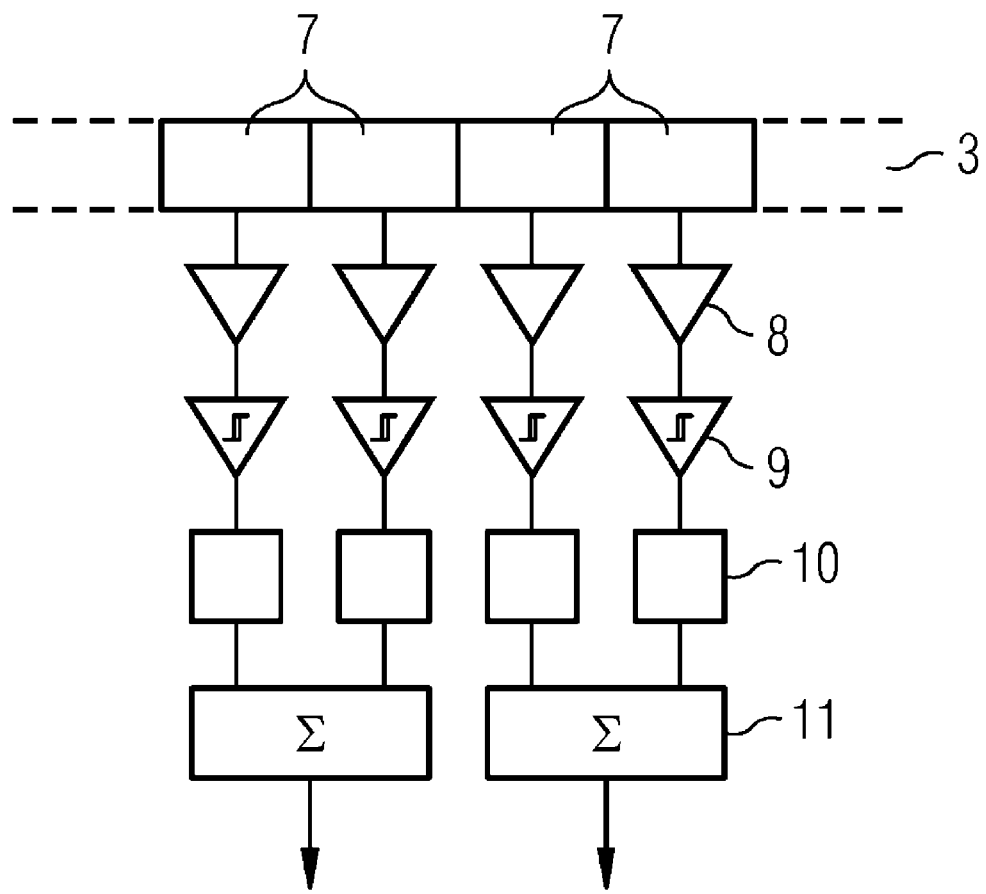

FIG. 5 shows a highly schematic example for the structure of a quanta-counting multichannel x-ray detector and its signal processing. The x-ray detector 3 consists of a plurality of detector elements 7, of which only four are shown by way of example in the figure. The x-ray quanta falling on each detector element 7 generate charge pulses because of the construction of the detector, which are amplified and shaped by the analog signal processing chain 8 and compared in a comparator 9 with adjustable threshold levels. If the set threshold levels are exceeded, a count pulse is created which is supplied to the counter 10. The count rates of this counter 10 for each detector element 7 or each channel are used in the proposed method for the evaluation.

If x-ray detectors are used in which a number of adjacent detector elements are combined to form a so-called macropixel, the count rates counted by each individual detector element of the macro pixel are combined. This is shown schematically in FIG. 5 for two detector elements combined into the macro pixel in each case by the summation units 11. Naturally it is also possible to already supply the count pulses of the combined detector elements to a common counter, so that then the summation units 11 are not needed. This step can naturally also run in a processing step through software outside the detector.

For the homogenization of the threshold values of such an x-ray detector with macro pixels formed from a number of detector elements the method is carried out in the same way for the individual channels or pixels and the target energy threshold is then set by means of dithering. The target energy threshold to be set in each case can be defined in this case with higher energy resolution than for the use of an x-ray detector without combined detector elements. If for example for individual pixels are combined and the target energy threshold was determined at 40.25 keV for a granularity of the thresholds of 1 keV, the threshold of one of the pixels is then set to 41 keV and the thresholds of the other three pixels to 40 keV. It is of no consequence which of the four pixels is set to 41 keV. 40.25 keV then produces an average threshold (in a linear approximation). This dithering can be improved if the approximation is not linear but the form of the spectrum and the individual quanta efficiency of the individual pixels is taken into account. In general, with the spectra which occur in practice however, a linear interpolation is already very suitable.

In an embodiment of the proposed method the effect of the dependence of the empty image on the spectrum of the incident x-ray radiation is used as an optimization criterion and in order, by variation of the electrical threshold levels of the individual channels and by minimization of the spectral dependence of the empty image, to reduce the threshold dispersion. The criterion is therefore precisely optimized, the deviation of which from the ideal case causes difficulties in further processing of the data, for example image artifacts. For the use of the x-ray detectors with combined detector elements or pixels the effective resolution of electronic thresholds can be improved by dithering. This functions especially well when the second measure of distance is given above is used, since this is especially well suited to the necessary interpolation.

To carry out an embodiment of the proposed method it is merely necessary to change the spectrum of the incident x-ray radiation. This can be done in almost all x-ray systems used in medicine by changing the acceleration voltage, by inclusion of filters in the beam path or by scanning a suitable phantom which effectively causes the incorporation of the various filters into the beam path, since these options are already present in the devices and thus no additional effort is required. The proposed method improves the result of the known calibration methods since it precisely minimizes the differences in the spectral sensitivity between the channels of a detector which lead to problems in the further processing of the image data. The method is not sensitive to differences in the sensitivity of the channels, for example because of the pixel size or differing quanta efficiency, and does not run the risk of compensating for the different sensitivities of the channels by changing the thresholds.

Although the invention has been illustrated and described in greater detail by the example embodiments, the invention is not restricted by the disclosed examples and other variations can be derived from said examples by a person skilled in the art without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for homogenization of threshold values of a multichannel, quanta-counting radiation detector including at least one comparator for each channel with an adjustable threshold value, the method comprising:

assigning at least one energy threshold, using the quanta-counting radiation detector, to the at least one adjustable threshold value of the at least one comparator;

carrying out, using the quanta-counting radiation detector, empty measurements with at least one different threshold value setting of the at least one comparator for different spectral compositions of the radiation; and determining, for each channel of which the at least one comparator is to be set to the same energy threshold, an adapted threshold value for the same energy threshold from the empty measurements at which a variation of a normalized count rate of the respective channel over the different spectral compositions of the radiation is reduced.

2. The method of claim 1, wherein the carrying out includes:

carrying out a first empty measurement for each of the different spectral compositions of the radiation at which the threshold values of the at least one comparator which are to be set to the same energy threshold, are set to a value assigned to the energy threshold, respective normalized count rates being calculated from the first empty measurements; and subsequently carrying out further empty measurements in a similar fashion in which the at least one threshold values of the at least one comparator is varied which are to be set to the same energy threshold, until a measure for a variation of the normalized count rates of the channel over the different spectral compositions of the radiation is reduced for each of the channels observed.

3. The method of claim 2, wherein the variation of threshold values in the further empty measurements is specified in each case by an algorithm.

4. The method of claim 1, wherein the count rates of the channels are each normalized to a value determined from the count rates of all channels of the respective empty measurement of which the at least one comparator is set to the same energy threshold.

5. The method of claim 1, wherein the count rates of the channels are each normalized to an average value, weighted average value, median or to another quantile from the count rates of all or some of the channels of the respective empty measurement of which the at least one comparator is set to the same energy threshold.

6. The method of claim 1, wherein the reduction of the variation of the normalized count rate of the respective channel is undertaken by the different spectral compositions of the radiation on the basis of the reduction of the variance of the normalized count rates over the different spectral compositions of the radiation.

7. The method of claim 1, wherein one of the spectral compositions is selected as the reference spectrum and the respective count rate of each channel of which the at least one comparator is set to the same energy threshold is normalized to a count rate of the same channel for which the empty measurement was normalized with the reference spectrum and the same setting of the at least one comparator.

8. The method of claim 7, wherein, for determining the adapted threshold value, a deviation of the normalized count rate of the respective channel from the normalized count rates of the other channels is reduced over the spectral compositions of the radiation of which the threshold values are set to this energy threshold.

9. The method of claim 1 for homogenization of threshold values of a multichannel quanta-counting radiation detector including, for each channel, at least one comparator with an adjustable threshold value, wherein count rates of a number of adjacent channels are combined to form a common channel, the method comprising:

setting at least two comparators of the common channel to different threshold values in order to obtain the threshold value for the common channel which lies between the energy thresholds of the at least two comparators.

10. The method of claim 2, wherein the count rates of the channels are each normalized to a value determined from the count rates of all channels of the respective empty measurement of which the at least one comparator is set to the same energy threshold.

11. The method of claim 2, wherein the count rates of the channels are each normalized to an average value, weighted average value, median or to another quantile from the count rates of all or some of the channels of the respective empty measurement of which the at least one comparator is set to the same energy threshold.

12. The method of claim 2, wherein one of the spectral compositions is selected as the reference spectrum and the respective count rate of each channel of which the at least one comparator is set to the same energy threshold is normalized to a count rate of the same channel for which the empty measurement was normalized with the reference spectrum and the same setting of the at least one comparator.

* * * * *